US008664450B2

(12) United States Patent
Aquino et al.

(10) Patent No.: US 8,664,450 B2
(45) Date of Patent: Mar. 4, 2014

(54) MANUFACTURE OF GAMMA-DELTA-UNSATURATED KETONES

(75) Inventors: Fabrice Aquino, Reiningue (FR); Werner Bonrath, Freiburg (DE); Rolf Kuenzi, Basel (CH)

(73) Assignee: DSM IP Assets B.V., Heerlen (NL)

( * ) Notice: Subject to any disclaimer, the term of this patent is extended or adjusted under 35 U.S.C. 154(b) by 295 days.

(21) Appl. No.: 13/125,083

(22) PCT Filed: Sep. 28, 2009

(86) PCT No.: PCT/EP2009/062486
§ 371 (c)(1),
(2), (4) Date: Apr. 20, 2011

(87) PCT Pub. No.: WO2010/046199
PCT Pub. Date: Apr. 29, 2010

(65) Prior Publication Data
US 2011/0213185 A1  Sep. 1, 2011

(30) Foreign Application Priority Data
Oct. 21, 2008  (EP) .................................. 08167181

(51) Int. Cl.
*C07C 49/20*  (2006.01)

(52) U.S. Cl.
USPC .......................... 568/408; 568/403

(58) Field of Classification Search
USPC .......................... 568/403, 398, 408
See application file for complete search history.

(56) References Cited

U.S. PATENT DOCUMENTS

| 6,034,279 A * | 3/2000 | Kashammer et al. | 568/391 |
| 6,380,437 B1 * | 4/2002 | Shi et al. | 568/405 |
| 6,586,635 B2 * | 7/2003 | Shi et al. | 568/322 |
| 2002/0161263 A1 * | 10/2002 | Shi et al. | 568/343 |
| 2010/0204520 A1 * | 8/2010 | Bonrath et al. | 568/403 |

FOREIGN PATENT DOCUMENTS

| JP | 11-152245 | 6/1999 |
| JP | 2001-504834 | 4/2001 |
| JP | 2007-520510 | 7/2007 |
| WO | WO 2005/075400 | 8/2005 |

OTHER PUBLICATIONS

International Search Report for PCT/EP2009/062486, dated Jun. 18, 2010.
Written Opinion for PCT/EP2009/062486, dated Jun. 18, 2010.
Saucy et al., "Uber die Reaktion von tertiaren Vinylcarbinolen mit Isopropylather. Eine neue Methode zur Herstellung von gamma-delta-ungesattigten Ketonen", *Helv. Chim, Acta.*, vol. 50, No. 7, Sep. 23, 1967, pp. 2091-2095.
Avrutski et al., "Study of the kinetics of methylheptenone synthesis under conditions of homegeneous acid catalysis", *Khimiko-Farmatsevticheskii Zhurnal*, vol. 15, No. 11, 1981.
Fujita et al, "Halogen Catalyzed Acetylenic Oxy-Cope Rearrangement in N-Methyl-2-Pyrrolidone Solvent a New Industrial Process for Pseudoionone and its Analogues," Tetrahedron Letters vol. 21, pp. 1347-1350, Pergamon Press Ltd, 1980, GB.

\* cited by examiner

*Primary Examiner* — Johann R Richter
*Assistant Examiner* — Pancham Bakshi
(74) *Attorney, Agent, or Firm* — Nixon & Vanderhye P.C.

(57) ABSTRACT

A process for the manufacture of gamma-delta-unsaturated ketones of formula $(R^1)(R^2)C=CH-CH_2-CH_2-CO-R^3$ (I), wherein $R^1$ is methyl or ethyl; $R^2$ is a saturated or unsaturated linear or cyclic hydrocarbon residue and $R^3$ is methyl or ethyl, by reacting a tertiary vinyl carbinol of formula $(R^1)(R^2)C(OH)-CH=CH_2$ (II) with an isopropenyl methyl or ethyl ether of formula $H_3C-C(OR^3)=CH_2$ (III) in the presence of an ammonium salt as catalyst.

5 Claims, No Drawings

MANUFACTURE OF GAMMA-DELTA-UNSATURATED KETONES

This application is the U.S. national phase of International Application No. PCT/EP2009/062486 filed 28 Sep. 2009 which designated the U.S. and claims priority to US Provisional Application No. EP Patent Application No. 08167181.0 filed 21 Oct. 2008, the entire contents of each of which are hereby incorporated by reference.

The present invention relates to a process for the manufacture of gamma-delta-unsaturated ketones of the general formula $(R^1)(R^2)C=CH-CH_2-CH_2-CO-R^3$ (I), wherein R1 is methyl or ethyl; R2 is a saturated or unsaturated linear or cyclic hydrocarbon residue and R3 is methyl or ethyl.

Saucy et al. (Helv. Chim. Acta 50, 2091-2095 (1967)) have described the preparation of gamma-delta-unsaturated ketones in high yields (73-94% relative to the carbinol) by reacting tertiary vinyl carbinols with isopropenyl ethers under pressure, at temperature of 120-200° C. during 12-16 hours, in the presence of catalytic amounts of phosphoric acid. Working without pressure resulted in far less yields, e.g., only 41% instead of 93% in case of 6-methyl-5-heptene-2-one (MH).

It has now surprisingly been found that compounds of formula I can be obtained in high yields if a tertiary vinyl carbinol of formula $(R^1)(R^2)C(OH)-CH=CH_2$ (II) is reacted with an isopropenyl methyl or ethyl ether of formula $H_3C-C(OR^3)=CH_2$ (III) in the presence of an ammonium salt as catalyst. It is an advantage to avoid acidic conditions in and to have available additional catalysts for the present addition reaction and subsequent rearrangement yielding the unsaturated ketones of formula I.

Saturated or unsaturated linear or cyclic aliphatic hydrocarbon residues comprise straight-chain or branched-chain alkyl, alkenyl and alkynyl groups with one or more double and/or triple bonds as well as cycloalkyl and cycloalkenyl groups, having 1 to 46 carbon atoms. Preferred examples of such groups $R^2$ are methyl, $CH_2$—prenyl, $CH_2$—geranyl, $CH_2$—farnesyl, $CH_2$—hexahydrofarnesyl, $CH_2$—solanesyl and $CH=CH-(2,6,6-trimethylcyclohex-1-enyl)$.

The starting compounds of formulae II and III, viz. the vinyl carbinols as well as isopropenyl methyl ether (IPM) and isopropenyl ethyl ether (IPE), are well-known in the art. They are commercially available or can be produced according to methods well-known in the art.

The ammonium salts useful in the present invention are ammonium salts of mineral acids, preferably ammonium bromide, ammonium chloride and di-ammonium phosphate. The salts can be used in amounts in the range of 0.1-10mol-%, preferably 0.5-5 mol-%, most preferably 1-2 mol-%.

The reactants can be used in equimolar amounts, however, it is preferable to use them in a molar range of 1.0:1.5-3.0, preferably 1:2.0-2.5 (II:III). The reaction can be carried out in the absence or presence of an inert solvent, e.g., .a hydrocarbon such as pentane, hexane or heptane. Preferably the reaction is carried out without solvent in an autoclave without additional pressure. With a reaction temperature in the range of 100-200° C., preferably 120-160° C., reaction time is normally in the range of 12-40 hours to achieve high conversion and good yields.

Isolation and work up of the desired product of formula I, including separation of isomers, if desired, is achieved by methods well-known in the art.

The invention is illustrated in more detail by the following Examples.

EXAMPLE 1

$NH_4Cl$ Catalyzed $C_3$-elongation of 3-methyl-1-butene-3-ol to 6-methyl-5-heptene-2-one Apparatus:

The main part is a stainless steel batch reactor from Medimex—High Pressure, number 910470 MED. 243 (build 1995), with a nominal volume of 1.0 liter, an operative temperature up to 220° C. and a maximum pressure of 20 bar. The heating system of the reactor is provided by electrical heating spirals located in the jacket. Cooling is obtained by water flowing through the reactor jacket. The temperature control comprises three thermocouples for the measurement of the inner reactor, jacket and cooling temperatures, with precision of ±0.05° C. A sensor measures the pressure with a precision of ±0.05 bars. The stirrer is a stainless steel four-propeller with a speed range from 0 to 1200 rpm, from Flender ATB-Loher (0.25 kW). The reactor is also connected to a safety and a data control system.

Procedure:

1.19 g of ammonium chloride (22.2 mMol=1.0 Mol %) were placed into the autoclave as described above. 198.5 g of 3-methyl-1-butene-3-ol (2.24 Mol) mixed with 349.1 g of IPM (4.70 Mol, 2.1 equiv.) were added. Total volume was 700 ml. The reactor was closed immediately and the stirrer was started (set on 500 rpm). The reaction mixture was heated to 150° C. within about 120 minutes. The experiment was carried out at isothermal conditions. After 12 hours reaction time the mixture was cooled down to 25° C. A sample of the brown reaction mixture was taken and analyzed by gas chromatography. Yield: 548.8 g reaction mixture methyl heptenone; conversion: 98.1%; selectivity: 1.0.

EXAMPLE 2

$NH_4Br$ Catalyzed $C_3$-elongation of Linalool to Geranylacetone

Apparatus: Same reactor as in Example 1.
Procedure:

1.736 g of ammonium bromide, 99% (17.55 mMol=1.5 Mol %), 184.8 g of linalool, 97.7 w % (1.17 Mol), and 218.6 g of IPM (96.5 area %, 2.925 Mol, 2.5 equiv.) were placed into the autoclave. Total volume was 500 ml. The reactor was closed immediately and the stirrer was started (set on 500 rpm). The reaction mixture was heated to 130° C. within about 100 minutes. The experiment was carried out at isothermal conditions. After a total reaction time of 40 hours the reaction mixture was cooled down to 22° C., drawn under vacuum out of the autoclave and stirred for 30 minutes with about 3 g of Na-acetate, followed by filtration over a 5 µm Teflon membrane. The low-boilers were removed at 20 to 30 mbar in a Rota vapor at 40° C.

Yield: 247.05 g brownish oil containing 79.9 w % geranyl acetone (mixture of E/Z-isomers). Conversion: 97.9%, yield: 86.8%, selectivity: 0.89.

EXAMPLE 3

$NH_4Cl$ Catalyzed $C_3$-elongation of Linalool to Geranylacetone

Apparatus: Same reactor as in Example 1.
Procedure:

1.26 g of ammonium chloride, 99% (23.4 mMol=2 Mo%), 184.8 g of linalool (97.7 w %, 1.17 Mol) and 218.6 g of IPM, 96.5 area % (2.925 Mol, 2.5 equiv.) were filled into the autoclave. Total volume was 500 ml. The reactor was closed immediately and the stirrer was started (set on 500 rpm). The reaction mixture was heated up to 140° C. within about 120 minutes. The experiment was carried out at isothermal conditions. After a total reaction time of 40 hours the reaction mixture was cooled down to 22° C., drawn under vacuum out of the autoclave and stirred for 30 minutes with about 3 g of Na-acetate, followed by filtration over a 5 μm Teflon membrane. The low-boilers were removed at 20 to 30 mbar in a Rota vapor at 40° C. The crude product was distilled in a 500 ml two-necked round-bottomed flask with a PT 100, oil bath, magnetic stirrer, Liebig-condenser, PT 100, Anschütz-Thiele separator, cold trap, high-vacuum pump. The pre-fraction was taken at $T_J$22-120° C., $T_H$22-40° C. and 0.07 mbar (on pump). The product fraction was taken at $T_J$120° C., $T_H$~93° C. and 0.02 mbar (on pump). Yield: 220.6 g of yellowish oil were obtained (95.8 w % geranyl acetate, total of E/Z-isomers). Conversion: 99.7%, yield: 93.1%, selectivity: 0.93.

EXAMPLE 4

$(NH_4)_2HPO_4$ Catalyzed $C_3$-elongation of Linalool to Geranylacetone

Apparatus: Same reactor as in Example 1.
Procedure:
  1.577 g of di-ammonium hydrogen phosphate (98%, 11.7 mMol=1.0 Mol %), 184.8 g linalool (97.7 w %, 1.17 Mol) and 218.6 g IPM (96.5 area %, 2.925 Mol, 2.5 equiv.) were filled into the autoclave. Total volume was 500 ml. The reactor was closed immediately and the stirrer was started (set on 500 rpm). The reaction mixture was heated to 150° C. within about 120 minutes. The experiment was carried out at isothermal conditions. After 30 hours reaction time the reaction mixture was cooled down to 22° C., and stirred for 30 minutes with about 3 g of Na-acetate, followed by filtration over a 5 μm teflon membrane. The low-boilers were removed at 20 to 30 mbar in a Rota vapor at 40° C. Yield: 243.9 g of brownish oil (81.5 w % geranyl acetate, mixture of E/Z-isomers). Conversion: 99.0%, yield: 87.4%, selectivity: 0.88.

EXAMPLE 5

$NH_4Br$ Catalyzed $C_3$-elongation of E-nerolidol to (All-E) and E/Z-Farnesyl Acetone Apparatus: described in Example 1.
Procedure:
  7.063 g of ammonium bromide, (99%, 71.4 mMol=9 Mol %) 178.5 g of E-nerolidol (98.8 area %, 0.793 Mol) and 225.8 g IPM (96.5 area %, 3.022 Mol, 3.81 eq) were placed into the autoclave. Total volume was 500 ml. The reactor was closed immediately and the stirrer was started (set on 500 rpm). The reaction mixture was heated up to 160° C. within about 120 minutes. The experiment was carried out at isothermal conditions. After a total reaction time of 16 hours the reaction mixture was cooled down to 22° C., and treated with triethylamine. The low-boilers were removed in two steps (10 mbar, 0.05 mbar on pump) in a Rota vapor at 40° C. The crude product was dissolved in about 500 ml of tert-butyl methyl ether and extracted 2× with 50 ml of water (total 100 ml). The organic layer was dried over $Na_2SO_4$ and filtered. The low-boilers were removed in two steps (10 mbar, 0.05 mbar on pump) in a Rota vapor at 40° C. The obtained product after extraction was distilled in a 500 ml two-necked round-bottomed flask with a PT 100, oil bath, magnetic stirrer, Liebig-condenser, PT 100, Anschütz-Thiele separator, cold trap, high-vacuum pump. The pre-fraction was taken at $T_J$22-140° C., $T_H$22-118° C. and 0.02 mbar (on pump). The product fraction was taken at $T_J$140° C., $T_I$127° C., $T_H$118-119° C. and 0.02 mbar (on pump). Yield: 36.2 g of yellowish oil were obtained as a pre-fraction with 68.3 area % farnesylacetone (total of all E and E/Z-isomers).
  169.4 g of a yellowish oil were obtained as a main-fraction with 98.3 area % farnesylacetone (total of all E and E/Z-isomers). Conversion: 99.1%, yield: 91.9%; selectivity: 0.93 (summarized fractions).

EXAMPLE 6

$NH_4Cl$ Catalyzed $C_3$-elongation of E-nerolidol to All E and E/Z-farnesyl Acetone Apparatus: Same reactor as in Example 1.
Procedure:
  1.714 g of ammonium chloride (99%, 31.7 mMol=4 Mol %), 178.5 g of E-nerolidol (98.8 area %, 0.793 Mol) and 225.8 g IPM (96.5 area %, 3.022 Mol, 3.81equiv.) were filled into the autoclave. Total volume was 500 ml. The reactor was closed immediately and the stirrer was started (set on 500 rpm). The reaction mixture was heated to 160° C. within about 120 minutes. The experiment was carried out at isothermal conditions. After a 16 hours reaction time the reaction mixture was cooled down to 22° C., and treated with triethylamine. The low-boilers were removed in two steps (10 mbar, 0.05 mbar on pump) in a Rota vapor at 40° C. The crude product was distilled in a 500 ml two-necked round-bottomed flask with a PT 100, oil bath, magnetic stirrer, Liebig-condenser, PT 100,Anschütz-Thiele separator, cold trap, high-vacuum pump. The pre-fraction was taken at $T_J$22-135° C., $T_H$22-95° C. and 0.04 mbar (on pump). The product fraction was . taken at $T_J$135-140° C., $T_I$110-126° C., $T_H$96-121° C. and 0.03 mbar (on pump).
  Yield: 199.8 gf yellowish oil were obtained containing 96.7 area % farnesyl aceton (mixture of (all-E) and E/Z-isomers). Conversion: 99.3%; yield: 92.8%; selectivity: 0.97.

EXAMPLE 7

$(NH_4)_2HPO_4$ Catalyzed $C_3$-elongation of E-nerolidol to (All-E) and E/Z-farnesyl Acetone Procedure:
  A 33 ml stainless steel autoclave equipped with a magnetic stirrer was charged with 5.36 g of E-nerolidol, 98.8 area % (0.024 Mol) and 6.77 g of IPM, 96.5 area % (0.091 Mol, 3.81 equiv.). Under stirring 24.05 mg of di-ammonium hydrogen phosphate, 98% (0.178 mMol=0.75 Mol %) were added. The closed autoclave was placed in a "Lab Shaker" with a heating block and shaken at 250 min$^{-1}$ for 16 hours at 160° C. (including 2 hours of heating-up). The autoclave was cooled down to RT over 1.5 hours in the heating block, opened and the reaction mixture was neutralized under stirring with triethylamine. The low-boilers were removed in two steps (10 mbar, 0.02 mbar on pump) in a Rota vapor at 40° C.
  Yield: 6.37 g of a yellowish oil as crude product was obtained containing 88.7 area % farnesyl acetone (total of all E and E/Z-isomers). Conversion: 95.9%; yield: 90.5%; selectivity: 0.94.

The invention claimed is:
  1. A process for the manufacture of gamma-delta-unsaturated ketones of formula (I):

$(R^1)(R^2)C=CH-CH_2-CH_2-CO-R^3$ (I), wherein $R^1$ is methyl or ethyl; $R^2$ is a saturated or unsaturated linear or cyclic hydrocarbon residue and $R^3$ is methyl or ethyl, wherein the process comprises reacting a tertiary vinyl carbinol of formula (II):

$(R^1)(R^2)C(OH)-CH=CH_2$ (II), with an isopropenyl methyl or ethyl ether of formula (III):

$H_3C-C(OR^3)=CH_2$ (III), in the presence of an ammonium ($NH_4^+$) salt as catalyst.

2. The process of claim 1, wherein the ammonium salt is ammonium bromide, ammonium chloride or di-ammonium-phosphate.

3. The process of claim 1, wherein the compound of formula (II) is 3-methyl-1-butene-3-ol.

4. The process of claim 1, wherein the compound of formula (II) is linalool.

5. The process of claim 1, wherein the compound of formula (II) is nerolidol.

\* \* \* \* \*